United States Patent [19]

Linkow et al.

[11] Patent Number: 4,908,030
[45] Date of Patent: Mar. 13, 1990

[54] METHOD OF MANUFACTURING SYNTHETIC BONE COATED SURGICAL IMPLANTS

[75] Inventors: Leonard I. Linkow, New York, N.Y.; Anthony J. Armini, Bedford, Mass.; Anthony W. Rinaldi, Philadelphia, Pa.

[73] Assignee: Vent-Plant Corporation, Inc., Philadelphia, Pa.

[21] Appl. No.: 43,908

[22] Filed: Apr. 29, 1987

[51] Int. Cl.[4] .......................... A61F 2/28; C23C 14/46
[52] U.S. Cl. .................................. 623/16; 204/192.11; 433/201.1
[58] Field of Search ..................... 204/192.15, 192.11; 623/16; 428/688; 433/201.1, 208; 427/2

[56] References Cited

U.S. PATENT DOCUMENTS 3,918,100 11/1975 Shaw et al. ................. 204/192.15 X

OTHER PUBLICATIONS

Kay, J. F. et al., (Abstract from the 12th Annual Meeting of the Society for Biomaterials, p. 13, 1986).
Cook, S. D, (Int. J. Oval and Maxillofacial Implants, 27:15–22, 1987).
Lacefield, W. R., (Abstracts from the 12th Annual Meeting of the Society for Biomaterials, p. 12, 1986).
Kent, J. N. et al., (Abstract from the 12th Annual Meeting of the Society for Biomaterials, p. 16, 1986).
Thomas, K. A. et al., (Abstracts from the 12th Annual Meeting of the Society for Biomaterials, p. 15, 1986).
J. L. Vossen et al., Thin Film Processes, Academic Press, New York, 1978, pp. 175–198.
J. L. Vossen et al., Thin Film Processes, Academic Press, New York, 1978, pp. 14–17, 42–45, 176.

Primary Examiner—John F. Niebling
Assistant Examiner—William T. Leader
Attorney, Agent, or Firm—Darby & Darby

[57] ABSTRACT

A process is provided for depositing hydroxylapatite on the surface of materials suitable for implantations into animals and humans. In this process, a coating of hydroxylapatite is applied to dental or surgical implants using a sputter technique that employs a high energy Xenon ion beam. The process is carried out in a vacuum into which a controlled amount of hydroxide ions are introduced.

15 Claims, 1 Drawing Sheet

METHOD OF MANUFACTURING SYNTHETIC BONE COATED SURGICAL IMPLANTS

BACKGROUND OF THE INVENTION

This invention relates to a novel method of manufacturing a synthetic bone-coated material useful for surgical and dental implants.

The mineral fraction of bones and teeth in vertebrates is composed largely of apatites (chemical formula $Ca_{10}(PO_4)_6OH_2$, in addition to carbonate, fluoride, hydroxide, and citrate. Bone crystals belong to the group of hydroxylapatites. These crystals are platelets, or rods, about 8 to 15 angstroms thick, 20–40 angstroms wide, and about 200–400 angstroms long, with a density of about 3.0. This inorganic crystal structure imparts to bone an elastic modulus similar in strength to that of concrete.

Synthetic hydroxylapatites (HA) have been developed and used for a variety of surgical purposes, e.g. to partially fill bone cavities and to promote the growth of new bone about HA fragments. Also, HA coatings have been formed on implant materials to promote the anchoring of the implant in bone.

The use of HA coating for biological implants offers several advantages. Hydroxylapatite (HA) has demonstrated its ability to enhance its integration into bone due to the fact that it biologically binds to natural bone. The deposition of new bone occurs on the HA coating itself leading to a significant increase in the rate at which the surgical site heals.

J. N. Kent, (*Abstracts from the 12th Annual Meeting of the Society for Biomaterials*, pp. 16, 1986), evaluated the efficacy of HA-coated and non-coated dental implants in dogs. Titanium cylindrical dental implants were coated with a fifty micron thick layer of HA and compared with non-HA coated titanium implants when placed in the anterior mandible and maxilla teeth for 12 weeks. Kent found that none of the non-coated materials adhered to the adjacent bone for any time period, whereas 100% of the HA-coated implants were adherent and could not be removed from the bone. The HA-coated implants demonstrated an intimate bone-implant interface without intervening fibrous tissue. The HA-coated dental implants thus provided an increased stability and retention over polished and grit surfaced cylindrical titanium dental implants.

Various techniques are known for the deposition of HA onto surfaces for use as biological implants. Thomas et al. (*12th Annual Meeting of the Society for Biomaterials.* pp. 15, 1986) disclosed that plasma-sprayed HA-coated porous titanium hip implants, that are inserted into adult mongrel dogs, demonstrate increased amounts of bone in growth as compared to non-HA coated implants. The coating was sintered HA about 50 microns thick, which was applied using a plasma spray technique. The bone adjacent to the HA coated implant also appeared to be better organized and had a higher degree of mineralization than the bone adjacent to control implants which lacked the HA coating.

Kay et al. (*Abstracts of the 12th Annual Meeting of the Society for Biomaterials*, pp. 13, 1986) disclosed the use of HA-coated smooth titanium and cobalt-chrome-molybdenum (Co-Cr-Mo) implants using a modified plasma spray process. Kay et al. report that the coating was of a high density; however, the outermost 15–20% of the coating was less dense due to the nature of the deposition process.

W. R. Lacefield, (*Abstracts of the 12th Annual Meeting of the Society for Biomaterials*, pp. 12, 1986) compared the coating of sintered alumina, titanium, and the alloys Ti-6Al-4V and Co-Cr-Mo by a dip process and by sputter coating using an Argon beam in a vacuum chamber. The dipping process comprised a repeated dipping of the test specimens in a slurry containing 3–5 mesh HA powder which was then fired at 1100–1200° C. for 1–3 hours. The sputter coating was accomplished by cleaning the materials first by use of an Argon ion beam, followed by sputter coating using a 6 inch diameter target of dense HA placed in the path of Argon ions (typically having energy of 2–3 kev) while the target was arranged on a rotating wheel. The sputter process was continued for 17–20 hours and produced a coating of 0.5–2.2 microns. Lacefield disclosed that dip coating had an adverse effect on the microstructure of the coated materials. This was due to an uncontrolled grain growth on the alumina, titanium and titanium alloy, and a massive carbide precipitation on the Co-Cr-Mo alloy. This led to low bone strengths and fracturing when the implant went from a high temperature (500° C.) to water. The sputter coated material, however, demonstrated a uniform thickness covering all topological features of the substrate and a high integrity of the HA coating. However, X-ray diffraction demonstrated that some sputter-coated implants had coatings which were not crystalline HA, but were primarily an amorphous calcium-phosphate layer.

All of the above prior art techniques suffer from the disadvantage that they form a brittle layer of deposited material which can easily break off. Additionally, the production of a rough and irregular coating by the prior art techniques can lead to irritation of the tissue in the area where the implant is applied, if growth occurs there. Moreover, the prior art techniques cannot be applied to threaded implant configurations such as screws or total hip replacements.

Therefore, what is needed is an improved process for coating materials for use in implants which overcomes the drawbacks and difficulties mentioned above in the prior art processes.

SUMMARY OF THE INVENTION

It is an object of the present invention to provide an improved process for manufacturing synthetic bone-coated implant material.

It is a further object of the present invention to provide a surgical implant material coated with HA for use in dental and surgical fields.

The present invention relates to an improved process for depositing HA on the surface of materials suitable for implantation into animals, particularly mammals (including humans). These materials, including but not limited to titanium alloys and cobalt-chrome-molybdenum alloys, are sputter coated with calcium hydroxylapatite using a high energy Xenon ion beam. This produces a coated surgical implant which is close to the proper hardness of natural bone and has an appropriate phosphate to calcium ratio. The HA is deposited as a thin layer which is not cracked or pitted.

In one embodiment, the present invention is used to apply a hydroxylapatite coating on dental or surgical implants. The Xenon ion beam has between 2 and 200 kev of energy and the entire process is conducted under a vacuum in the presence of a preselected amount of water vapor.

BRIEF DESCRIPTION OF THE DRAWINGS

The foregoing and other features of the present invention will be apparent to those of ordinary skill in the art in light of the present description, accompanying claims and appended drawings in which:

DETAILED DESCRIPTION OF THE INVENTION

Figure 1:
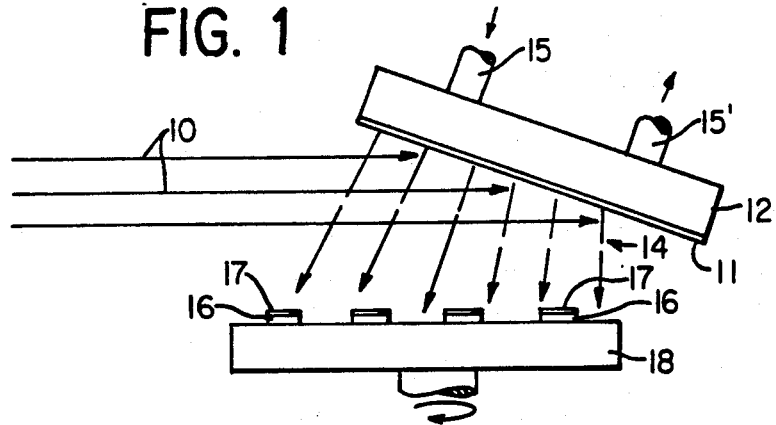
FIG. 1 is a drawing of the apparatus used in the practice of the present invention.

The present invention is directed to an improved process for depositing HA onto the surface of materials suitable for dental or surgical implants. The process employed for this coating is ion beam sputtering, which uses a high energy ion beam to "kick out" atoms from a HA plate and allows them to be directed onto the device to be coated. The geometry of this setup is shown in FIG. 1.

A 50 kev Xenon beam 10 is directed at an angled substrate 12 containing a coating 11 of sintered HA. The substrate 12 may be hollow and water cooled by a flow of water into conduit 15 and out of conduit 17, which are connected to the hollow interior of the substrate 12. The striking of the beam 10 onto the coating 11 leads to the sputtering of HA ions 14 out of the coating 11 onto parts 16 which are to be coated. These parts are placed upon a rotating support platter 18 that may also be water cooled. The entire arrangement is located in a high vacuum into which a controlled amount of oxygen or, preferably, water vapor is bled. As a result, a thin coating 17 of HA is formed on the product. This sputter process may be utilized on implant materials that cannot survive the high temperatures of vacuum evaporation which has been used in the prior art for coating materials with HA.

The high velocity imparted to the sputtered atoms through the use of a high energy Xenon beam directed at an HA target allows the atoms to penetrate into the surface of the device to be coated and, therefore, provides a superior adhesion of HA to the parts over those produced using evaporative coating techniques.

Xenon ion beam sputtering is a process that provides extremely high microscopic temperatures (high kinetic energy) while maintaining the macroscopic temperature of the bulk HA below its sublimation/decomposition point. Without this capability, less energy would be imparted to the target and thus the ions would not penetrate the surface of the device to be coated to the same extent. This would produce a coating that does not have the adherence of the present invention.

The ion beam used in this process, preferably Xenon, impels atoms out of the target substrate onto the surface of an implant part or material 16. Xenon is preferred because it can produce a high energy beam which reacts chemically with the substrate and produces a higher yield of sputtered HA than any other readily-available gas.

An alternative to the use of the Xenon beam includes, but is not limited to a Krypton beam. As used herein, high energy is defined as at least 2 kev and may extend up to 200 kev, but preferably is at least 10 kev.

The substrate 12 (FIG. 1) is covered with a suitable target coating material 11, preferably sintered HA. Alternative target coating materials include, but are not limited to, plasma sprayed HA and HA powder. The process is carried out in a high vacuum so that contaminant atoms cannot be incorporated into the growing film. A high vacuum, as used herein, is defined broadly as at least $10^{-4}$ torr to $10^{-7}$ torr and preferably from $10^{-6}$ torr to $10^{-7}$ torr.

A proper stoichiometry of the HA compound is achieved by bleeding into the vacuum a precisely metered amount of oxygen or preferably water vapor such that OH groups are formed to replace some of the oxygen that is usually lost from the HA molecule while in transit to the metal substrate. The amount of oxygen to be used broadly falls within the range of between about $10^{-5}$ torr and about $10^{-6}$ torr, and preferably within the range of between the ranges of $3 \times 10^{-6}$ torr and $9 \times 10^{-6}$ torr. It is related to the vacuum pressure used. The amount of water vapor to be used would be twice as much as the above-cited amounts for oxygen.

Figure 2:
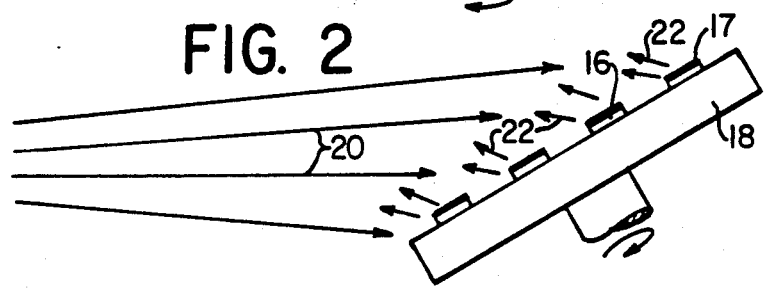
FIG. 2 is a drawing of the apparatus used to ion beam etch the material to be sputter coated.

Prior to the coating process, the metal substrate can first be sputter-etched or cleaned by directing the ion beam directly onto the metal surface to be coated. The arrangement of the apparatus to accomplish this is shown in FIG. 2. Xenon ions 20 are impelled onto the parts 16 to be coated. The entire operation is conducted in a vacuum upon the rotating water-cooled platter 18 (Model Z-100 ion implanter, available from Eaton Corp., Beverly, MA). This action sputters off all surface oxides 22 and permits the HA molecules deposited as shown in FIG. 1 to adhere directly to the metal surface with no intervening oxide barrier.

Figure 3:
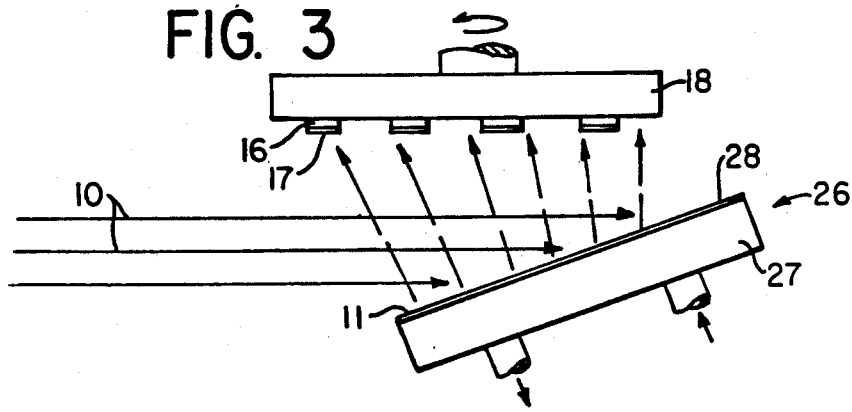
FIG. 3 is a drawing of the apparatus used in an alternative embodiment of the present invention.

An alternative to the deposition process of FIG. 1 is shown in FIG. 3. In this process, the target 26 and the parts 16 have been reversed in position so that the target is below the parts. The target in this arrangement is made in the form of a tray 27 supporting powdered HA 28, instead of sintered HA. Since the powder is loose and is not adhered to the target substitute 26, the creation of a target is simple and inexpensive. However, the target must be right side up or the powdered HA would fall off.

Because of the high energy of the Xenon beam, the HA ions are given sufficient energy to kick off the target against the force of gravity, reach the parts and still have sufficient velocity to penetrate the surface of the parts.

The principal uses of the present invention are for any application where live bone must grow toward and adhere to a foreign metal within the body of an animal or human to be treated. This includes total joint prosthesis, dental implants, ear implants, and similar devices.

The advantages of the process of the present invention include the ability to coat a metal substrate with HA which is close to natural apatite ($Ca_{10}(PO_4)_6(OH)_2$). This is in part achieved through the introduction of OH ions into the atmosphere of the vacuum. In addition, crystal grains are not visible on the coating surface, thus leading to a featureless surface having a full density non-porous HA film. This eliminates the tendency of the film to crack when the implant is bent as is often necessary during installation. Also, the process leads to an excellent adhesion of the HA material to titanium, stainless steel, cobalt-chrome-molybdenum and similar materials, while keeping the production costs at a minimum.

S. D. Cook et al (*Int. J. Oral and Maxillofacial Implants*, 27: 15–22, 1987) disclosed that plasma sprayed HA Coated titanium implants developed 5–8 times the mean interface strength of uncoated material when implanted into adult mongrel dogs. Histological evaluations in all cases revealed mineralization of interface bone directly onto the HA-coated implant surface. However, push-out tests conducted at all times post-implantation, demonstrated that failures occurred primarily at the HA-titanium interface. Therefore, HA-coated implants of the present invention can be further coated, using a conventional plasma spray or modified plasma spray process (such as those disclosed in U.S. Pat. Nos. 4,145,764 issued Mar. 27, 1979 and 4,223,412 issued Sept. 23, 1980, both incorporated herein by reference). This would lead to a titanium implant with two layers of HA-coating. The one micron thick, ion-implanted HA coating would act as an intermediate layer to effect a method of bonding subsequently plasma sprayed HA coatings to titanium. The resultant implant would then have the advantages of superior biocompatability and superior adhesion of both methods.

The present invention is described further below in specific examples which are intended to illustrate it without limiting its scope.

EXAMPLE 1

The sputtering experiments described below were done using a modified ion implanter (Eaton Model Z-100, Eaton Corp., Beverly, MA).

The Xenon ion beam current on the water-cooled HA sputter target was approximately 2mA over an area of approximately 16 in.$^2$ on the HA. The samples which were used were microscope glass slides, and small (1 cm. diameter) stainless steel metal discs which were masked with a sheet of stainless steel foil to cover half of the exposed area. Runs were performed using approximately 20 mA-hours of Xenon dose and using none, $3 \times 10^{-6}$ torr, and $6 \times 10^{-6}$ torr oxygen gas bled into the vacuum chamber.

The target was a copper plate of 4 inches ×4 inches × ¼ inch thick, coated with approximately 75 microns of sintered HA (Coor's, Inc., Golden, Colorado).

The results of a series of three runs are prescribed in Table 1 below.

TABLE 1

| Run # | Ion Beam Dose | O$_2$ Pressure | Samples |
|---|---|---|---|
| 1 | 20 mA-hrs. | 0 | 1-Glass Slide<br>1-Stainless Disk<br>1-Titanium Foil |
| 2 | 20 mA-hrs. | $3 \times 10^{-6}$ torr | 1-Glass Slide<br>1-Stainless Disk |
| 3 | 20 mA-hrs. | $6 \times 10^{-6}$ torr | 1-Glass Slide<br>1-Stainless Disk |

The thickness of each film was determined using a step profiling machine (Sloan-Dektak, Santa Barbara, CA). The films were all approximately 5,000 Angstroms (0.5 micron) thick and were translucent as seen on the coated glass slides. On the metal pieces, they were greenish due to the preferential reflection of green light at that particular thickness. The average sputter rate was 233A/mA-hr. for all three runs.

A scanning electron microscopic (SEM) analysis demonstrated that even under 10,000 × magnification, the HA films were essentially featureless, which indicates that they are not porous, have nearly-full density and have no grain boundaries.

An elemental x-ray analysis using Edax (Amry, Bedford, MA) was performed. The X-rays emitted during the electron examination give an indication of the elements present above the atomic number of sodium. The spectrum of elements in the sample on the titanium foil demonstrated that Ti, Al, and V from the metal, as well as P, Cl, and Ca from the HA coating were present. The percentage of phosphorous and calcium (in atomic percents) in the sample film was 32% and 68%, respectively. When a natural apatite standard was analyzed on the same instrument, the values for phosphorous and calcium were 35% and 65%, respectively. This result demonstrates that the process of the present invention is capable of producing a coating which is very close to natural apatite.

A hardness analysis was performed upon the coated material. The mineral HA has a hardness of 5 on the Mohs scale (diamond is 10 and talc is 1 on this scale). Measurements with calibrated scratch points demonstrated that a Mohs 4 did not scratch the film, a Mohs 5 barely scratched it and a Mohs 6 probe severely scratched it. The hardness is therefore about 5 from this measurement, which is consistent with a fully dense HA.

The adhesion of the HA film to both titanium and stainless steel appeared to be extremely good from additional scratch tests that were performed. These scratch tests demonstrated no flaking or transverse cracks along the scratch line, even at a 200 fold magnification. This shows that the adhesion to metal is as good or better than the shear strength of the material itself.

EXAMPLE 2

The sputtering apparatus as described above in Example 1 was employed and the target was a cold pressed HA powder, 2"×4"×⅛", formed at a pressure of 500 psi using the techniques and apparatus described above.

Films coated on glass and single crystal sodium chloride plates were analyzed by X-ray diffraction in order to ascertain the obtained crystal structure. The results demonstrated that the sputtered films were essentially dense, amorphous HA. However, upon subsequent vacuum annealing in a conventional utility furnace at $10^{-4}$ torr pressure and at temperatures ranging between about 300° C. and about 900° C., for times ranging between about 1 hour and 24 hours, complete recrystallization occurred.

The invention has been described in reference to preferred embodiments. It will be obvious to those of ordinary skill in the art that many additions, substitutions and deletions can be made without departing from the spirit and scope of the invention as claimed below.

What is claimed is:

1. A process for manufacturing hydroxylapatite-coated implants comprising the steps of:
   obtaining an implant material suitable for implantation into an animal,
   ion beam sputter coating said implant material with hydroxylapatite by directing a Xenon ion beam operated at at least 10 kev energy against a hydroxylapatite target positioned such that hydroxylapatite ions kicked off of the target strike the implant material,
   conducting said ion beam sputter coating under a vacuum of at least $10^{-4}$ torr in the presence of a preselected amount of a molecular oxygen-containing gas, recovering said hydroxylapatite-coated implant annealing said hydroxylapatite-coated implant in a vacuum at a pressure of at least $10^{-4}$ torr from about 1 hour to about 24 hours at a temperature ranging between about 300° C. and about 900° C., and recovering a completely recrystallized hydroxylapatite-coated implant.

2. The process of claim 1 wherein said metal implant is sputter-etched prior to said ion beam sputter coating.

3. The process of claim 1 wherein the Xenon ion beam is directed substantially horizontally, the implant material is located below the beam, and the target is positioned in the path of the beam such that HA ions are directed down onto the implant material.

4. The process of claim 3 wherein the implant material is located on a water cooled rotating platter.

5. The process of claim 3 wherein said hydroxylapatite target comprises a solid hydroxylapatite coating on a water cooled substrate.

6. The process of claim 3 wherein said hydroxylapatite target comprises a sintered hydroxylapatite coating on a water cooled substrate.

7. The process of claim 1 wherein said implant material is selected from the group consisting of titanium, titanium alloys, stainless steel and cobalt-chrome-molybdenum.

8. The process of claim 7 wherein said hydroxylapatite target comprises powdered hydroxylapatite located on a water cooled tray.

9. The process of claim 1 wherein said molecular oxygen containing gas is present in amounts such that oxygen present is in the range from about $10^{-5}$ torr to about $10^{-6}$ torr.

10. The process of claim 1 wherein said molecular oxygen-containing gas comprises water vapor under said vacuum.

11. The process of claim 10 wherein said molecular oxygen-containing gas is present in amounts such that the oxygen present is in the range from about $10^{-5}$ torr to about $10^{-6}$ torr.

12. The process of claim 1 wherein the Xenon ion beam is directed substantially horizontally, the implant material is located about the beam, the target is positioned in the path of the beam such that HA ions are directed up onto the implant material.

13. The process of claim 1, wherein said hyroxylapatite-coated implant is plasma spray coated with a second hydroxylapatite layer.

14. A hydroxylapatite-coated implant, suitable for implantation into an animal in need of such treatment, manufactured by a process comprising the steps of:

obtaining an implant suitable for implantation into an animal, ion beam sputter coated said implant with hydroxylapatite by directing a Xenon ion beam operated at at least 10 kev energy against a hydroxylapatite target positioned such that hydroxylapatite ions kicked off of the target strike the implant, conducting said ion beam sputter coating under a vacuum of at least $10^{-5}$ torr in the presence of a preselected amount of a molecular oxygen containing gas, recovering said hydroxylapatite coated implant, annealing said hydroxylapatite-coated implant in a vacuum at a pressure of at least $10^{-4}$ torr for from about 1 hour to about 24 hours at a temperature ranging between about 300° C. and about 900° C., and recovering said hydroxylapatite-coated implant, the hydroxylapatite coating being fully dense, crystalline and substantially the same in terms of percentages of phosphorous and calcium as natural hydroxylapatite.

15. The implant of claim 14 wherein the implant is plasma spray with a second hydroxylapatite layer prior to the step of recovering.

* * * * *